United States Patent
Liley (10) Patent No.: US 8,483,815 B2
(45) Date of Patent: Jul. 9, 2013

(54) EEG ANALYSIS SYSTEM

(75) Inventor: David Tibor Julian Liley, Yarraville (AU)

(73) Assignee: Cortical Dynamics Limited, North Perth (AU)

( * ) Notice: Subject to any disclaimer, the term of this patent is extended or adjusted under 35 U.S.C. 154(b) by 1141 days.

(21) Appl. No.: 12/303,736

(22) PCT Filed: Jun. 6, 2007

(86) PCT No.: PCT/AU2007/000801
§ 371 (c)(1),
(2), (4) Date: Mar. 25, 2009

(87) PCT Pub. No.: WO2007/140536
PCT Pub. Date: Dec. 13, 2007

(65) Prior Publication Data
US 2011/0184305 A1    Jul. 28, 2011

(30) Foreign Application Priority Data
Jun. 6, 2006 (AU) ................. 2006903073

(51) Int. Cl.
*A61B 5/04* (2006.01)
(52) U.S. Cl.
USPC ....................................... 600/544
(58) Field of Classification Search
None
See application file for complete search history.

(56) References Cited

U.S. PATENT DOCUMENTS

| | | |
|---|---|---|
| 5,010,891 A | 4/1991 | Chamoun |
| 5,083,571 A | 1/1992 | Prichep |
| 5,797,853 A | 8/1998 | Musha et al. |
| 6,067,467 A | 5/2000 | John |
| 6,549,804 B1 | 4/2003 | Osorio et al. |

FOREIGN PATENT DOCUMENTS

WO   WO 2004/064633 A1   8/2004

OTHER PUBLICATIONS

Schack et al (Brain Topography, 1995, 8(2): 127-136).*
Schack B, et al (1995). Dynamic Power and Coherence Analysis of Ultra Short-Term Cognitive Processes—A Methodical Study. Brain Topography, 8(2), p:127-136, pp. 129-131.
Schack B, et al (1995). Methods of dynamic spectral analysis by self-exciting autoregressive moving average models and their application to analyzing biosignals. Medical & Biological Engineering & Computing, 33, p:492-498, pp. 493-496.
L. Patomaki et al., Tracking of nonstationary EEG with the roots of ARMA models, Engineering in Medicine and Biology Society, vol. 2(20), pp. 877-878,Kuopio, Finland, (1995).
P. Gannabathula et al., ARMA order selection for EEG—an empirical comparison of three order selectin algorithms, The Annual International Conference of the IEEE Engineering in Medicine & Biology Society, vol. 5, pp. 1686-1687, 1989, Bangalore, India.

* cited by examiner

*Primary Examiner* — Sean Aeder
(74) *Attorney, Agent, or Firm* — Zarley Law Firm, P.L.C.

(57) ABSTRACT

A process for analysing an electroencephalogram signal representative of activity of a brain, including: i) generating coefficient data for a signal representation of a portion of said signal; ii) generating first gain data representing an average amplitude of an output signal generated based on said signal representation and said coefficient data; iii) generating second gain data representing an average amplitude of said portion; and iv) generating, based on said first gain data and said second gain data, brain state data representing subcortical activity of said brain.

16 Claims, 6 Drawing Sheets

EEG ANALYSIS SYSTEM

FIELD

The present invention relates to a process and system for analysing electroencephalogram (EEG) signals to generate a display representing activity of a brain.

BACKGROUND

A process for quantifying the functional state of the brain may involve analysing the spontaneous or stimulus locked scalp recordable electrical activity from a subject. This may involve analysing the waveform of early, middle and/or late stimulus evoked components (e.g. as described in International Patent Publication WO2001/74248); or spectral analysis of spontaneously recorded activity (not in response to a particular or general stimulus) using frequency or time domain methods (e.g. as described in European Patent Application EP0898234); or a hybrid approach in which both spontaneous and evoked EEG activity is analysed to determine brain state (e.g. as described in International Patent Publication WO2004/054441).

While such methods have been shown to have clinical efficacy when appropriately constructed statistical discriminant functions are employed, it is unclear what physiological aspects of behaviour and brain function such measures reflect. For instance, it may be changes in EMG activity and not EEG activity that are being detected with these approaches. The Messner report (published in Anesth Analg, 2003, 97, pp. 488-491) describes how the bispectral index declines during neuromuscular blockade in fully awake persons. However, recent theoretical and experimental work by Liley et al (as described in International Patent Publication WO2004/064633 and the references referred to therein) on the biological mechanisms responsible for the production of rhythmic scalp recordable brain electrical activity provides a specific theoretical framework that enables the construction of more physiologically specific measures of brain function. In assessing the state of the brain during health, disease and/or therapeutic intervention, it is important to distinguish changes in brain state that occur as a result of altered brain (cortical) function and those changes that occur as a consequence of altered input to the cerebral cortex. While an analysis of the early components of a variety of event related potentials (ERP) may provide information regarding the integrity of the various input pathways to the cortex, this technique is necessarily limited as not all cortical areas are the recipient of peripherally derived sensory information. For example, the frontal cortex neither directly nor indirectly (through subcortical nuclei) receives any sensory information. Another limitation of this approach is that, in order to obtain a sufficient signal-to-noise ratio, the evoked response of a number of sequentially presented stimuli must be determined which clearly limits the temporal resolution of the results obtained. However, there are methods that attempt to improve the temporal resolution by using some form of forecasting method (e.g. as described in International Patent Publication WO2001/74248).

Quantitative EEG (QEEG) methods involving spectral analysis using time or frequency domain methods (e.g. as described in European Patent Application EP0898234) are unable to distinguish between changes in cortical input and brain (cortical) state, because such techniques are unable to make assumptions regarding the physiological sources of changes in EEG spectral power. This is principally a consequence of the heuristic approach of current QEEG methods.

Accordingly, it is difficult to determine whether changes in EEG signals from a subject are caused by changes in cortical input (e.g. to different areas of the brain), or are a consequence of qualitative and quantitative changes in how cortex responds to this input.

It is therefore desired to address one or more of the above, or to at least provide a useful alternative.

SUMMARY

According to the present invention there is provided a process for analysing an electroencephalogram signal representative of activity of a brain, including:

i) generating coefficient data for a signal representation of a portion of said signal;

ii) generating first gain data representing an average amplitude of an output signal generated based on said signal representation and said coefficient data; iii) generating second gain data representing an average amplitude of said portion; and iv) generating, based on said first gain data and said second gain data, brain state data representing subcortical activity of said brain.

The present invention also provides a system for analysing an electroencephalogram signal representative of activity of a brain, including a processor module adapted to:

i) generate coefficient data for a signal representation of a portion of said signal;

ii) generate first gain data representing an average amplitude of an output signal generated based on said signal representation and said coefficient data; iii) generate second gain data representing an average amplitude of said portion; and iv) generate, based on said first gain data and said second gain data, brain state data representing subcortical activity of said brain.

The present invention also provides computer executable code stored on computer readable medium to perform any of the steps in a process as described above.

The present invention also provides a system for performing a process as described above.

BRIEF DESCRIPTION OF THE DRAWINGS

A preferred embodiment of the present invention is herein described, by way of example only, with reference to the accompanying drawings, wherein.

DETAILED DESCRIPTION OF THE PREFERRED EMBODIMENTS

Figure 1:
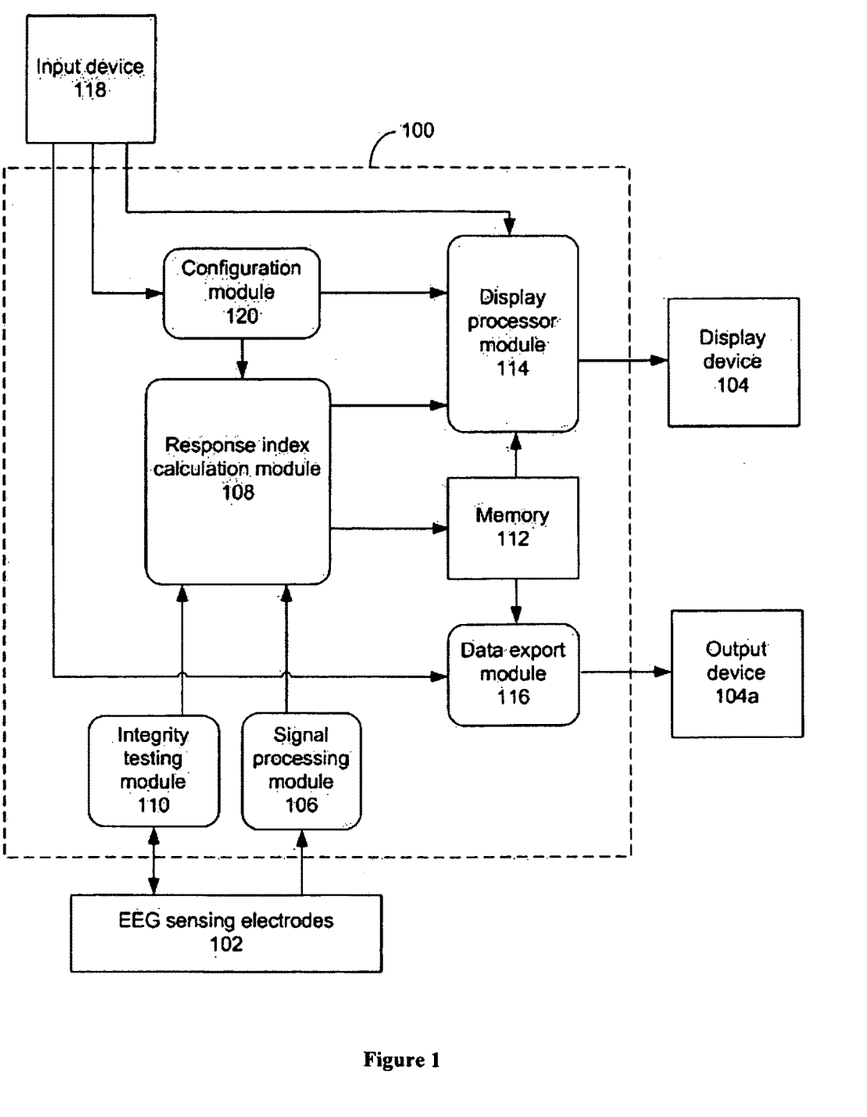
FIG. 1 is a block diagram of the components in the EEG processing system.

The electroencephalogram (EEG) processing system 100, as shown in FIG. 1, includes a signal processing module 106, response index calculation module 108, integrity testing module 110, memory module 112, display processor module 114, data export module 116, and configuration module 120. The modules 106 and 110 are coupled to a plurality of scalp electrodes 102 placed on the subject's scalp. The electrodes 102 are positioned on the subject's scalp in accordance with the international 10:20 standard system, and may include use of additional mid-point electrodes as required. For example, the electrodes 102 may be attached to a strip that positions the electrodes relative to a mid-point of the subject's forehead. Whilst the electrodes 102 are preferably referenced to linked ears and are attached to an electrode cap that uses the nasion as a ground, other electrode arrangements can be used. The electrodes 102 detect an EEG signal from the subject's scalp, which is then received and processed by the EEG processing system 100.

The components of the EEG processing system 100 may be implemented in software and executed on a standard computer running a standard operating system (such as Microsoft Windows™ or Unix). Those skilled in the art will also appreciate that the processes performed by the components can also be executed at least in part by dedicated hardware circuits, e.g., Application Specific Integrated Circuits (ASICs) or Field-Programmable Gate Arrays (FPGAs). The components of the system 100 may be implemented as a combination of hardware, embedded firmware and software.

The signal processing module 106 receives and amplifies an EEG signal detected by the electrodes 102, and performs preliminary signal artefact rejection by filtering low frequency movement artefact, electromyogram (EMG) artefact and/or mains interference noise (generally ranging from 20 Hz to 75 Hz) from the EEG signal. For example, the module 106 may filter the detected EEG signal using a 50-60 Hz notch filter before applying a band-pass filter (e.g. a low-pass filter) to the signal somewhere on the range 0 Hz to 60 Hz. The module 106 then generates digital samples representative of the EEG signal using standard analog-to-digital conversion components. The EEG signal may be digitised at a fixed rate (such as between 128 to 512 samples per second), and preferably, at no less than 14-bit resolution.

The response index calculation module 108 may perform further signal artefact rejection, including removing additional artefacts from the digital EEG signal not removed by the signal processing module 106 which may compromise the subsequent estimation of the ARMA model coefficients. This involves further removing 50-60 Hz mains contamination using a variety of means or algorithms, such as least mean square adaptive filtering.

The response index calculation module 108 then stores the samples in memory 112 and processes the samples in accordance with a processing option selected by the user. A user may select a processing option that controls the response index calculation module 108 to store samples generated for an EEG recording session, and to retrieve and process the stored samples. The processing performed by module 108 involves generating a plurality of segments, each including a predetermined number of sequential samples (e.g. representative of a 2-second portion of the EEG signal). Module 108 may generate segments based on an incremental (or "sliding window") approach, for example, by generating a new segment at predetermined time intervals so that each new segment includes one or more new samples generated by the signal processing module 106 as well as samples previously generated by the module 106. Module 108 generates, based on the respective samples for each segment, a time invariant autoregressive moving average (ARMA) representation of the EEG signal for each segment (e.g. based on Equation 2). Module 108 then generates brain response data for each segment based on the respective time invariant ARMA representations.

The brain response data for each segment/EEG sample point includes (i) coefficient data representing autoregressive (AR) coefficients and moving average (MA) coefficients; (ii) poles data representing the position of one or more poles on a complex plane determined based on the coefficient data; (iii) zeros data representing the position of one or more zeros on a complex plane determined based on the coefficient data; and (iv) mean pole data representing a mean position of poles determined from the poles data.

The user may select a different processing option that controls the response index calculation module 108 to store the samples in memory 112 and to process the samples based on a recursive approach. The processing performed by module 108 involves generating a time varying ARMA representation of a portion of the EEG signal for each sequential sample point of the EEG signal. A sample point may correspond to each respective sample generated by module 106, or alternatively, module 108 selects new sample points at predetermined time intervals. Module 108 generates coefficient data for each sample point respectively based on a fixed order time varying ARMA representation of the EEG signal that depends on the sampled EEG signal values for the current sample point and for a number of previous sample points, and the coefficient data corresponding to the previous EEG sample point, in a recursive manner (e.g. based on Equation 3). Module 108 then generates poles data, zeros data and/or mean pole data for each sample point based on the corresponding coefficient data for that sample point.

The processing performed by module 108 includes generating AR coefficients and MA coefficients for the ARMA representation for each segment/sample point, and each of the ARMA representations has an AR order of between 8 and 13 and a MA order between 5 and 11. However, the ARMA representation preferably has an AR order of 8 and MA order of 5. The AR and MA coefficients generated for each segment/sample point enables the corresponding ARMA representations (when using the AR and MA coefficients as parameters) to represent the EEG signal for the corresponding segment/sample point.

The samples in each segment represent a different portion of the EEG signal, and the samples in adjacent segments may overlap and represent a common portion of the EEG signal. For example, a segment may include 50% of the samples included in another segment immediately preceding it. The degree of overlap of samples in adjacent segments may vary, and a greater degree of overlap (e.g. having more than 50% of the samples in common) enables better estimation of the AR and MA coefficients. Thus, a more accurate representation of the subject's brain function and/or the level of subcortical input/activity can be provided on the basis of the AR and MA coefficients.

The response index calculation module 108 then generates index data and product data for each segment/sample point based on the corresponding brain response data, and stores the index data and product data in memory 112. The product data represents a product value which represents the level of cortical input to the subject's brain, and which is generated based on the EEG samples, coefficient data, and ARMA representation for the corresponding segment/sample point. The product value may be scaled to fall within a predefined range (e.g. from 0 to 100 inclusive, based on Equations 13 or 14). A larger product value represents a greater level of cortical input to the subject's brain, and a smaller product value represents a lower level of cortical input.

The index data represents an index number that represents the functional state of the subject's brain (i.e. the way in which the brain responds to subcortical input to the brain) and which is generated based on the mean pole data. The index number may be scaled to fall within a predefined range (e.g. from 0 to 100 inclusive, based on Equations 13 or 14). A decrease or inhibition to brain function (e.g. caused by introducing an anaesthetic agent to the subject that decreases cortical response) results in module 108 generating a small index number to represent a lower functional state of the brain. For example, an index number of 0 represents no brain activity. Where brain function is normal or is uninhibited (e.g. during a normal alert state of mind without interventions affecting the cortex), this results in module 108 generating a large index number to represent a higher functional state of the brain. For example, an index number of 100 represents the brain at a fully awake state. Changes in the functional state of the subject's brain can be determined by the changes in the value of the index number for different segments/windows. An advantage of the present invention is that the assessment of brain function of a subject takes into account the degree of brain activity caused by the inherent cortical state.

Figure 3:
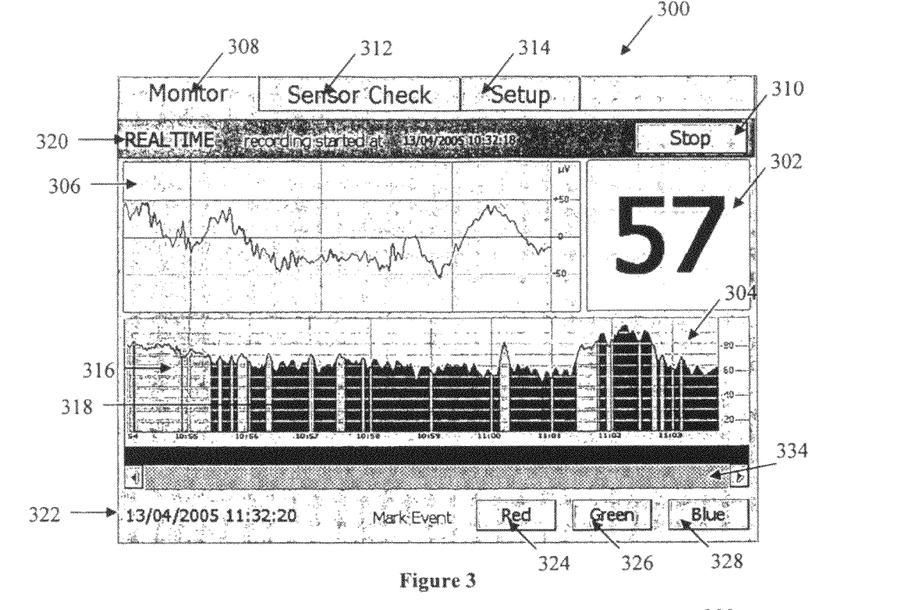
FIG. 3 is an EEG recording interface of the system.
Figure 7:
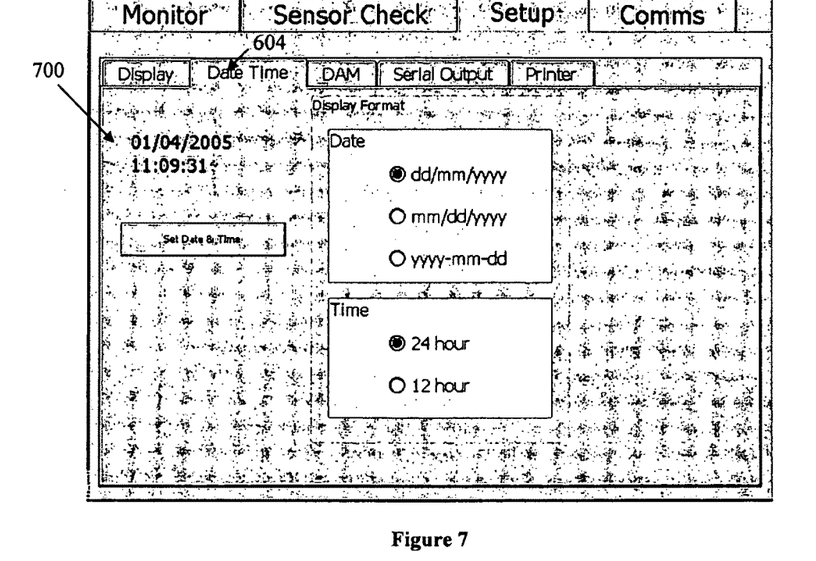
FIG. 7 is a date/time setup interface of the system.

The response index calculation module 108 passes the brain response data, index data and/or product data (collectively referred to as brain state data) to the display processor module 114 for generating display data representing one or more user interface displays for the display device 104 (e.g. a CRT or LCD display). The display processor module 114 may receive user input from an input device 118 (e.g. a multi-key data entry device or mouse) whilst generating display data for the display device 104. In one embodiment, the input device 118 and display device 104 are combined into one I/O device (e.g. a touch screen display) so that the display processor module 114 receives user input from, and sends display data to, the same I/O device. The display processor module 114 may also generate one or more display interfaces based on the brain response data, index data and/or product data retrieved from memory 112. FIGS. 3 and 7 are examples of user interface displays generated by module 114.

FIG. 3 is an EEG recording interface 300 generated by the display module 114 when the processing an EEG signal using the sliding windows option. The interface 300 includes a monitor tab 308, sensor check tab 312 and setup tab 314 for accessing user interfaces associated with different functions performed by the EEG processing system 100. The interface 300 is generated under the monitor tab 308, and includes a brain response index 302 generated based on the index data, a brain response graph 304 representing changes in the value of the brain response index 302 over time, and an EEG graph 306 representing the detected EEG signal generated based on the EEG samples. The interface 300 includes a control button 310 that enables a user to start and stop an EEG recording/monitoring session performed by the EEG processing system 100. The interface 300 also includes fields for displaying information, such as a date/time field 322 displaying the current date/time, and a status field 320 for displaying the processing option selected by the user and the creation date/time for the record data currently displayed on the interface 300. The interface 300 includes an adjustable scroll bar 334 which enables a user to select a viewing portion of graphs 304 and/or 306 for display on the interface 300.

The interface 300 may include one or more event marker buttons 324, 326, 328 for recording an event associated with each respective button. For example, button 324 may be used for indicating the time at which the subject loses consciousness under anaesthesia, and button 326 may be used for indicating the time at which the subject regains consciousness. Each button 324, 326, 328 is associated with a different colour, and when a button 324, 326, 328 is selected by the user, a line of the corresponding colour is generated on the brain response graph 304 corresponding to the time at which the button was operated. The time positions of events recorded on the brain response graph 304 are stored in memory 112.

The brain response graph 304 of the recording interface 300 is generated based on the brain response index 302 such that a portion of the graph 304 is generated for display in a colour corresponding to a predetermined range of response index 302 values, where each predefined range is represented by a different colour. For example, if the index 302 is between 0 and 20 (inclusive), the corresponding area under the graph 304 is displayed in a first colour (e.g. in blue). If the index 302 is between 21 and 40 (inclusive), the corresponding area under the graph 304 is displayed in a second colour (e.g. in dark green, shown as item 318 in FIG. 3). If the index 302 is between 41 and 60 (inclusive), the corresponding area under the graph 304 is displayed in a third colour (e.g. in light green). If the index 302 is between 61 and 80 (inclusive), the corresponding area under the graph 304 is displayed in a fourth colour (e.g. in orange, shown as item 316 in FIG. 3). If the index 302 is between 81 and 100 (inclusive), the corresponding area under the graph 304 is displayed in a fifth colour (e.g. in red). The recording interface 300 may include a similar graph generated based on the product data, for example, a portion of the graph is generated for display in a colour corresponding to a predetermined range of product values, where each predefined range is represented by a different colour.

Figure 4:
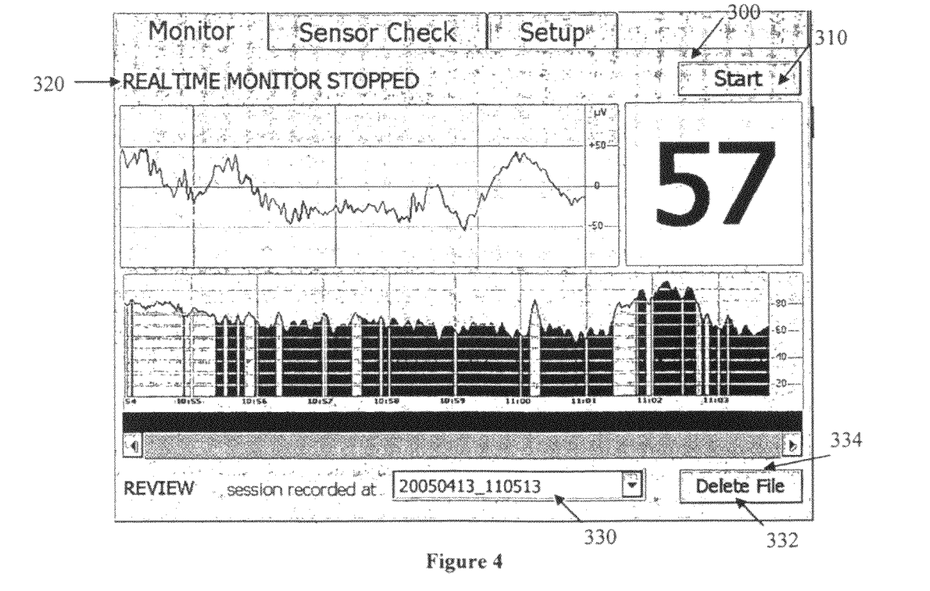
FIG. 4 is an EEG recording interface of the system in the review state.

FIG. 4 is the EEG recording interface 300 in the review state, i.e. when a user has operated the control button 310 to stop the system 100 from processing EEG signals. As shown in FIG. 4, the status field 320 displays a message indicating that processing has stopped. The interface 300 also includes a delete button 332 for deleting data associated with the recent EEG recording from memory 112, and a storage location field 330 (e.g. as a drop down menu) for a user to specify the storage location (e.g. file path and name) and/or parameters for exporting data associated with the recent EEG recording.

Figure 5:
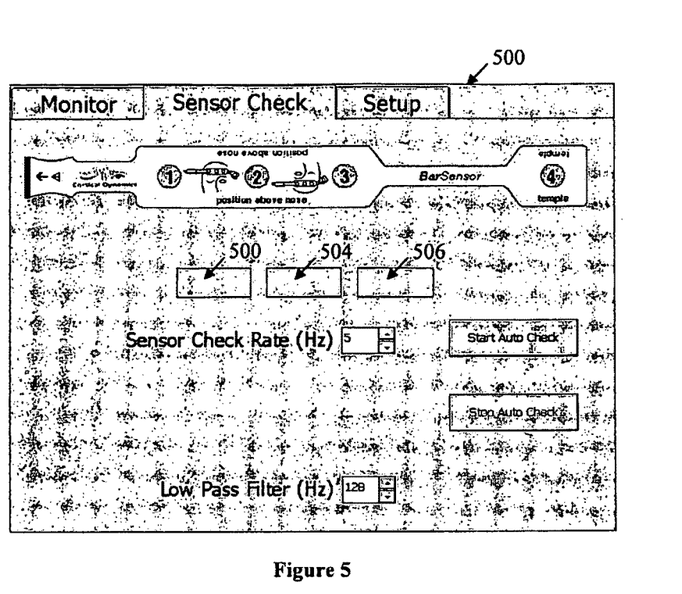
FIG. 5 is a sensor diagnostic interface of the system.

FIG. 5 is a sensor diagnostic interface 500 generated by the display module 114 when a user selects the sensor check tab 312. The diagnostic interface 500 enables a user to control a diagnostic process for verifying the operational status of the electrodes 102. The system 100, under the control of the diagnostic process, measures the impedance between each respective electrode and comparing it to a reference value. The diagnostic interface 500 includes a flag 502, 504, 506 corresponding to each respective electrode, and a flag for a particular electrode is coloured if the electrode has impedance outside a range (e.g. if it is greater than 5-10 kOhms) necessary for accurate performance.

Figure 6:
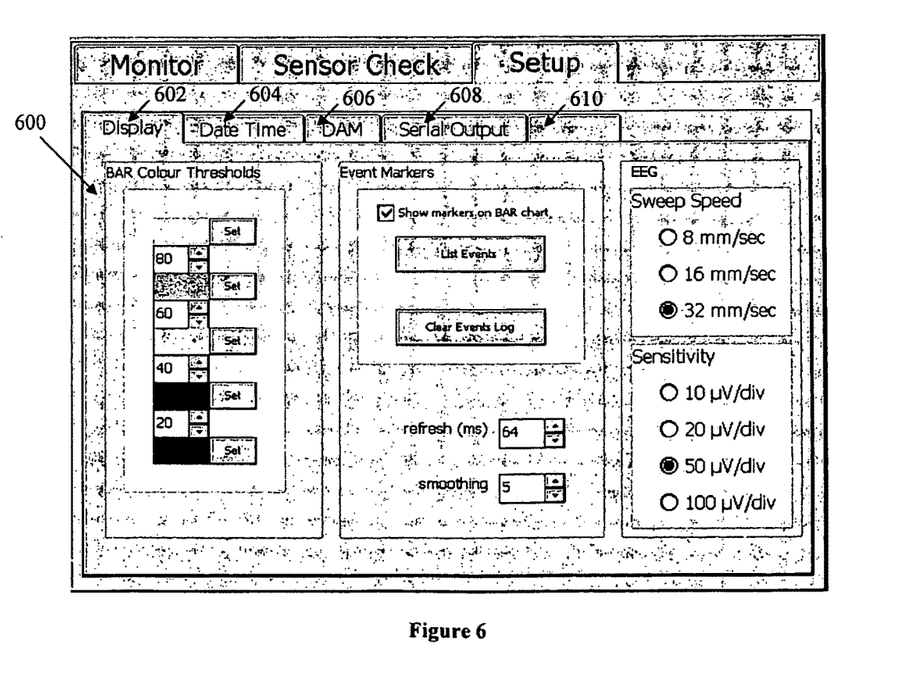
FIG. 6 is a setup interface of the system.

FIG. 6 is a setup interface generated by the display module 114 when a user selects the setup tab 314. The setup interface includes a display setup tab 602, date/time setup tab 604, system configuration tab 606, output setup tab 608 and a printer setup tab 610 for accessing user interfaces for configuring operating parameters of the EEG processing system 100. The display module 114 generates a display setup interface 600 when a user selects the display setup tab 602. The interface 600 includes fields for a user to select and/or configure each of the threshold brain response index levels/ranges and their corresponding colours; the events associated with each event marker button 324, 326, 328; the display refresh rate; display smoothing parameters; and the sweep speed and sensitivity (i.e. amplitude) of the brain response graph 304 and/or EEG graph 306.

FIG. 7 is a date/time setup interface 700 generated by the display module 114 when a user selects the date/time setup tab 604. The interface 700 includes fields for a user to select and/or configure the system clock date/time display format.

Figure 8:
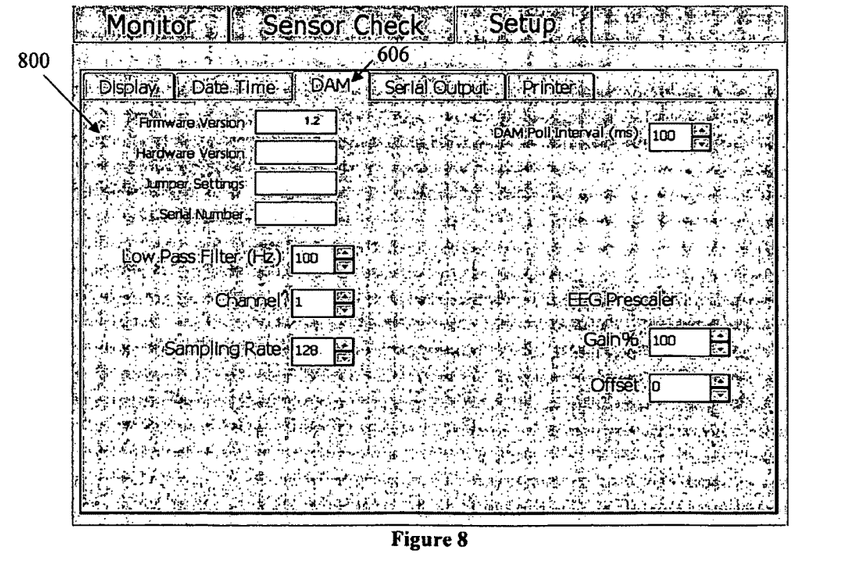
FIG. 8 is a system configuration interface of the system.

FIG. 8 is a system configuration interface 800 generated by the display module 114 when a user selects the system configuration tab 606. The interface 800 includes display fields for displaying the serial number, hardware version number, firmware version number, and jumper settings of the system 100. The interface 800 includes fields for a user to select and/or configure parameter values for the low pass filter, the channels for detecting EEG signals, the sampling rate, the polling interval (e.g. in milliseconds), and parameters for prescaling the EEG samples for display on the EEG graph 304.

Figure 9:
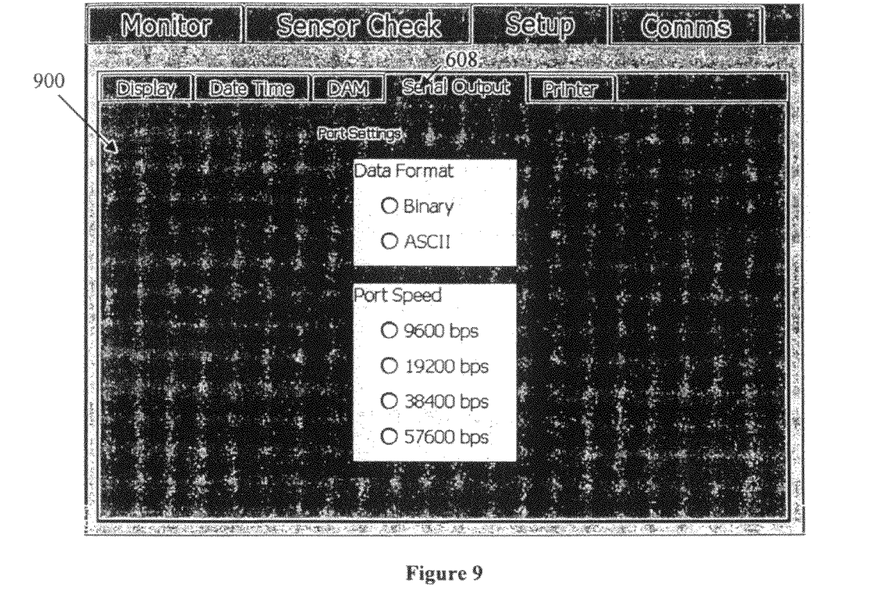
FIG. 9 is an output setup interface of the system.

FIG. 9 is an output setup interface 900 generated by the display module 114 when a user selects the output setup tab 608. The interface includes fields for a user to select and/or configure the type and/or format of the output data generated by the data export module 116, and the port speed (e.g. for a serial port) of the data export module 116. Output data generated by the data export module 116 is transferred to an output device 104a (e.g. a printer, disk drive, USB port, serial/parallel port, etc.). Output data generated by the data export module 116 may represent:

i) a patient status report (e.g. including graphs, charts, a summary description of the patient's brain function status, and/or changes of this status over time);

ii) a signal output representative of a recorded EEG signal; and/or iii) a data file including any of the features described above.

The display module 114 generates a printer setup interface when a user selects the printer setup tab 610, which includes user adjustable fields for selecting and configuring the type and/or format of the output data generated by the data export module 116 for an output device 104a (e.g. a printer).

The configuration module 120 of the EEG processing system 100 receives user input from the input device 118, and generates configuration data for controlling the operation of the response index calculation module 108 and the display processor module 114. The configuration data includes control signals, parameters and/or instructions that controls modules 108 and/or 114 to perform one or more of the following:

i) select a processing option for processing the EEG samples;

ii) define the degree of overlap between adjacent segments/windows; iii) configure module 108 to store the EEG samples, brain response data, index data and/or product data in memory 112;

iv) define the display characteristics of user interfaces generated by the display module (e.g. including the layout of the interface displays, screen size, screen refresh rate, sweep speed and sensitivity of graphs displayed, brain response index threshold ranges and corresponding colours, smoothing settings, etc.)

v) define date and time settings;

vi) define event marker settings (e.g. including the number and type of events associated with each event marker button, and the colour associated with each type of event);

vii) define date export settings (e.g. including the type, format and/or transmission speed of data output to be generated by the data export module 116); and/or viii) define, select or configure other operation parameters of the system 100 (such as the sensor check rate, and the band-pass filter range (Hz) for the filtering performed by modules 106 and 108).

The integrity testing module 110 continually evaluates the detected EEG signal from the electrodes 102 by comparing the signal against expected parameters (e.g. raw EEG RMS amplitude in the range 2 to 100 microvolts, and 90% of EEG power between 0 and 30 Hz) in order to determine the operational status of the electrodes 102.

An EEG signal detected from a subject can be analysed on the basis of a theoretical assumption that the EEG signal is the result of a filtered random process. As described in International Patent Publication WO2004/064633, an EEG signal detected from a subject could be described mathematically as Equation 1:

$$H_e(\omega; q) = \frac{N(\omega; q)}{D(\omega; q)} P(\omega) \qquad \text{Equation 1}$$

where $H_e$ represents the EEG signal in the frequency domain, and P represents the input into the subject's cortex from other parts of the brain which can be used to assess the functional state of the cortex. N and D define polynomials in $\omega$, the roots of which determine the dominant frequencies of the EEG signal. $P(\omega)$ is assumed to represent Gaussian white noise, and is therefore independent of the frequency $\omega$ (i.e $P(\omega)=P_0$ is a constant that is theoretically determined as been proportional to subcortical input). In Equation 1, q represents a list of physiological parameters that theoretically determine the coefficients of the polynomials in $\omega$ for both the numerator N and denominator D.

The EEG signal for each respective segment/sample point can be expressed as a respective ARMA time series representation, and more advantageously, as a respective fixed order ARMA time series representation with an autoregressive order of 8 and a moving average order of 5. Equation 2 is a difference equation representing a (8,5) order ARMA representation for generating a representation of a portion of an EEG signal:

$$y[n] = -\sum_{k=1}^{8} a_k y[n-k] + \sum_{k=0}^{5} b_k u[n-k] \qquad \text{Equation 2}$$

where y[n] represents an ordinal sequence of sampled EEG signal values (i.e. y[n] is the n-th sequential sample), y[n−k] represents the k-th prior sampled value of y[n]; u[n−k] represents a Gaussian white noise process; and $a_k$ and $b_k$ is included in the coefficient data and respectively represent the AR (autoregressive) coefficients and MA (moving average) coefficients for a portion of an EEG signal corresponding to a segment. Estimates of the AR and MA coefficients can be generated in a number of ways, for example, using the ARMASA Matlab Toolbox application by P. M. T. Broersen of Delft University of Technology, or using any other ARMA modelling software package.

A time invariant ARMA representation of an EEG signal, as shown in Equation 2 can be re-written as a time varying ARMA time-series representation of an EEG signal as shown in Equation 3:

$$y[n] = -\sum_{k=1}^{8} a_k^{(n)} y[n-k] + \sum_{k=0}^{5} b_k^{(n)} u[n-k] \quad \text{Equation 3}$$

The AR and MA coefficients for Equation 3, represented by $a_k^{(n)}$ and $b_k^{(n)}$ respectively, are expressed a function of time (for time instant n). By denoting Equations 4 and 5:

$$\theta_n = (-a_1^{(n)}, \ldots, -a_8^{(n)}, b_1^{(n)}, \ldots, b_5^{(n)})^T \quad \text{Equation 4}$$

$$\phi_n = (y_{n-1}, \ldots, y_{n-8}, u_{n-1}, \ldots, u_{n-5})^T \quad \text{Equation 5}$$

Equation 3 can be re-written in state-space form as Equation 6:

$$y_n = \phi_n^T \theta_n + u_n \quad \text{Equation 6}$$

where $\phi_n^T$ represents a regression vector, $\theta_n$ represents model parameters (or states) corresponding to those in Equation 4, and $u_n$ represents a Gaussian white noise process corresponding to $u[n-k]$ in Equation 3. By assuming that the model parameters $\theta_n$ evolve as a random walk when no a priori information is available, $\theta_n$ can be estimated recursively from previous values of $\theta_n$ and $y_n$ according to the following general scheme shown in Equation 7:

$$\hat{\theta}_n = \hat{\theta}_{n-1} + K_n \epsilon_n \quad \text{Equation 7}$$

where $K_n$ and $\epsilon_n$ represent the recursively determined filter gain and prediction error of the ARMA model estimated at the previous sample point of the EEG signal, respectively. A variety of methods are available to recursively generate estimates of the time varying AR and MA coefficients $\theta_n$. For example, it is possible to generate coefficient data based on a Kalman adaptive filtering method (e.g. as described in Tarvainen et al, *Estimation of non-stationary EEG with Kalman smoother approach: an application to event-related synchronization (ERS)*, IEEE Trans Biomed Eng, 2004, 51, pp. 516-524), or based on any other recursive processing method (e.g. a recursive processing method as described in Ljung L., *System Identification—Theory for the User*, Prentice Hall, Upper Saddle River, N.J. 2$^{nd}$ edition 1999), or using software (e.g. the functions associated with the MATLAB® System Identification Toolbox version 6.0), to generate optimal estimated values (e.g. in the mean square sense) for the model parameters in $\theta_n$ (expressed as $\hat{\theta}_n$).

Equations 2 and 3 can be rewritten in the z-domain notation, as shown in Equation 8:

$$Y(z) = \frac{\sum_{k=0}^{5} b_k z^{-k}}{\sum_{k=0}^{8} a_k z^{-k}} U(z) \quad \text{Equation 8}$$

where Y(z) represents an ARMA representation of a portion of the EEG signal in the z-domain; U(z) represents a Gaussian white noise process in the z-domain; and the coefficients $a_k$ and $b_k$ respectively correspond to the AR and MA coefficients for the corresponding segment/sample point. In general, the estimation of ARMA coefficients involves defining $b_0$ and $a_0$ as unity.

The poles associated with the system described by Equation 8 correspond to the roots of the denominator in Equation 8. The poles data for each segment/sample point are generated based on Equation 9 using the coefficient data for the corresponding segment/sample point (where the poles are represented by p). There are 8 possible solutions (or poles) to Equation 9, not all of which are necessarily distinct.

$$\sum_{k=0}^{8} a_k p^{-k} = \sum_{k=0}^{8} a_k p^{8-k} = 0 \quad \text{Equation 9}$$

The zeros associated with the system described by Equation 8 correspond to the roots of the numerator in Equation 8. The zeros data for each segment/sample point are generated based on Equation 10 using the coefficient data for the corresponding segment/sample point (where the zeros are represented by z). There are 5 possible solutions (or zeros) to Equation 10, not all of which are necessarily distinct.

$$\sum_{k=0}^{5} b_k z^{-k} = \sum_{k=0}^{5} b_k z^{5-k} = 0 \quad \text{Equation 10}$$

The poles and zeros represented by the data generated based on Equations 9 and 10 are complex numbers. The poles and zeros for each respective segment/sample point can be plotted on a z-plane, where a change in the position of one or more of the poles and/or zeros represents a change in the level of subcortical input to the subject's brain, and a change in a mean position of the poles represents a change in the functional state of the subject's brain. However, it is technically quite difficult to quantify the functional state of a brain based on the movement of one or more of the poles and/or zeros.

As described in International Patent Publication WO2004/064633, it is expected that various pharmacological interventions result in the motion of a subset of the poles of Equation 8 when plotted in a complex plane (or z-plane). It is possible to quantify the motion of a subset of the poles by generating a value representative of the mean motion of all of the poles represented by the data generated based on Equation 8. In particular, it is found that the mean real part of the pole motion is particularly sensitive to pharmacological manipulation/intervention to a brain.

$$\bar{z}_p \equiv \sum_{i=1}^{i=8} z_{i,p} \quad \text{Equation 11}$$

In Equation 11, $z_{i,p}$ represents the i-th pole and accordingly $\bar{z}_p/8$ represents the mean pole location on a complex plane. Because poles $z_{i,p}$, if complex, exist in complex conjugate pairs $\bar{z}_p/8$ will always be real. Mean pole data is generated based on Equation 12:

$$\bar{z}_p = a_1 \quad \text{Equation 12}$$

As a consequence of the properties of polynomials, the mean pole location can be determined from the first AR coefficient generated based on Equation 2 (represented as $a_1$) by dividing the $a_1$ coefficient by 8. However, because the mean pole location is to be scaled to form an appropriate index (i.e. a numeric value that, for example, ranges from 0 to 100) it is not necessary to perform this division to obtain the mean pole location. But instead, it is possible to determine the effect of changes in the mean pole location based on the value of $\bar{z}_p$ itself. Because $\bar{z}_p/8$ will always be greater than or equal to –1 and less than or equal to 1 it can be appropriately scaled so that it extends over the interval 0 to 100. For instance $\bar{z}_p$ may be linearly scaled based on Equation 13 to give an index representative of cortical activity or function:

$$\text{index} = c - m\bar{z}_p \qquad \text{Equation 13}$$

where c and m are constants chosen to ensure that index lies in some pre-defined range. $\bar{z}_p$ may also be nonlinearly scaled to give an index representative of cortical activity or function based on Equation 14:

$$\text{index} = \frac{d}{1 + e^{-a(\bar{z}_p - b)}} \qquad \text{Equation 14}$$

where a, b and d are constants chosen to ensure that the index lies in some pre-defined range. Index data for each respective segment/sample point represents an index number is generated based on either Equation 13 or Equation 14 using the mean pole data for the corresponding segment/sample point.

The unscaled mean real pole value represented by the mean pole data for each respective segment/sample point is plotted as a graph (e.g. graph 304 in FIG. 3) to show changes in the unsealed mean real pole value as a function of time or relative to the corresponding segment/sample point number. The unsealed mean real pole is expected to either increase or decrease in response to therapeutic intervention or disease. Alternatively, the mean real pole and the other AR and MA coefficients may be processed by a suitably defined and constructed discriminant function to produce a single scalar quantity representing the functional state of a brain. Such a discriminant function can be determined via stepwise discriminant analysis using any number of commercially available statistical packages for example Systat (Systat Software Inc, Richmond, USA).

The theoretically derived transfer function shown in Equation 1 can be rewritten in a factored canonical form as Equation 15:

$$H_e(\omega; q) = \frac{g(q)\prod_{k=1}^{k=5}[i\omega - z'_k(q)]}{\prod_{k=1}^{k=8}[i\omega - p'_k(q)]} P(\omega) \qquad \text{Equation 15}$$

where $P(\omega)$ represents the level of cortical input to the brain. Due to the expected temporal complexity of cortical input in the actual cortex, such input is assumed to be indistinguishable from, and representative of, a Gaussian random (white noise) process, i.e $P(\omega) = P_0$. In Equation 15, values for each of the 8 poles (represented by $p'_k$) and 5 zeros (represented by $z'_k$) are determined based on a number of physiological parameters (represented by q). The values of $z'_k$ for Equation 15 are generated based on Equation 16 using the zeros data generated based on Equation 10. The values of $p'_k$ for Equation 15 are generated based on Equation 17 using the poles data generated based on Equation 9.

$$z'_k = f_s \ln|z_k| + f_s Arg(z_k)/2\pi \qquad \text{Equation 16}$$

$$p'_k = f_s \ln|p_k| + f_s Arg(p_k)/2\pi \qquad \text{Equation 17}$$

where $f_s$ is the EEG sampling (digitization) frequency. In Equation 15, g(q) represents a gain factor that depends explicitly on one or more of the parameters represented by q. In theory, it is expected that the value of g(q) for a subject remains generally unchanged both before and during the application of an intervention to the subject (e.g. an anaesthetic agent) which affects the functional state of the cortex. Accordingly, the value of g(q) is assumed to be a constant. The product $g(q)P(\omega)$ can be used to estimate the level of cortical input to the subject's brain, and since g(q) is assumed to be a constant, it is expected that any changes in the value of $g(q)P(\omega)$ are caused by changes in $P(\omega)$.

The EEG processing system 100 generates product data based on Equation 18 representing the product $g(q)P(\omega)$ from Equation 15, based on the assumption that $P(\omega)$ represents Gaussian white noise:

$$g(q)P(\omega) = \frac{\langle \tilde{Y}(t) \rangle}{\langle Y(t) \rangle} \qquad \text{Equation 18}$$

where $\langle \tilde{Y}(t) \rangle$ represents an average signal amplitude of a portion of an EEG signal (e.g. of a selected segment of an EEG signal); and $\langle Y(t) \rangle$ represents an ARMA gain value for the corresponding portion of the EEG signal. The value of $\langle \tilde{Y}(t) \rangle$ can be determined as the root mean square (RMS) of the amplitude of the EEG signal for a selected segment/sample point. The ARMA gain value $\langle Y(t) \rangle$ can be determined as the RMS of the amplitude of a signal representation of the EEG signal for the selected segment/sample point.

The AR and MA coefficients for a selected segment is generated based on a time-invariant ARMA representation (i.e. based on Equation 2), so a signal representation of the EEG signal for that segment is generated based on Equation 2. The signal representation represents a sequence of values generated based on Equation 2 (i.e. y[n] in Equation 2), where the output of Equation 2 is generated based on the AR and MA coefficients for the selected segment, when driven by a normalised white noise input (i.e. where u[n−k] represents random values determined by a zero mean unit variance Gaussian random process).

The AR and MA coefficients for a selected sample point is generated based on a time-varying ARMA representation (i.e. based on Equation 3), a signal representation of the EEG signal for that sample point is generated based on Equation 3. The signal representation represents a sequence of values (i.e. y[n] in Equation 3), where the output of Equation 3 is generated based on the AR and MA coefficients for the selected sample point, when driven by a normalised white noise input (i.e. where u[n−k] represents random values determined by a zero mean unit variance Gaussian random process).

ARMA gain can be generated in a number of ways, for example, using the arma2cor function of the ARMASA Matlab Toolbox application by P. M. T. Broersen of Delft University of Technology, or using any other ARMA modelling software package.

Equations 2 and 3 represent a fixed order (8,5) ARMA representation of a portion of an EEG signal. Although an ARMA representation having an autoregressive order of 8 and moving average order of 5 is expected to give the best results, other AR and MA orders can be selected.

Theoretically, the gain factor, g, depends on the parameters, q, according to Equation 19:

$$g \cong \frac{\exp(1)\psi_e[h^*_e(q)]\gamma_e}{\tau_e} \qquad \text{Equation 19}$$

and thus cortical input, $P(\omega)$, can be estimated using Equation 20:

$$P(\omega) \cong \frac{\tau_e \langle \tilde{Y}(t) \rangle}{\exp(1)\psi_e[h_e^*(q)]\gamma_e \langle Y(t) \rangle} \quad \text{Equation 20}$$

where, in Equations 19 and 20, $\psi_e[h^*_e(q)]$ represents the efficacy of excitation in cortex (and which is proportional to the transmembrane driving force for excitatory activity at rest), $\gamma_e$ represents the corresponding rate constant for excitation, and $\tau_e$ represents the effective passive membrane time constant. In mean field modelling, the respective values for $\psi_e[h^*_e(q)]$, $\gamma_e$ and $\tau_e$ during intervention are not expected to be significantly perturbed from their undisturbed values. The cortical input, $P(\omega)$, determined using Equation 20, together with the poles and zeros obtained from the coefficients $a_k$ and $b_k$ generated based on Equations 2 or 3, represents a more comprehensive linear characterisation of the dynamics of the EEG signal detected from the subject.

Thus, armed with knowledge about how a particular pharmaceutical agent affects single neuronal physiological properties, of which there is extensive information, the technique disclosed herein can be used to determine variations in input to the brain that are affected by said pharmaceutical agents. This is of particular relevance when it is considered that a variety of pharmaceutical agents known to affect brain function have sites and targets of action that are distributed throughout the central nervous system.

For example, nitrous oxide is both a hypnotic and analgesic agent and is known to affect sites cortically and subcortically (e.g. as discussed in Hopkins P M, *Nitrous oxide: a unique drug of continuing importance for anaesthesia*, Best Pract Res Clin Anaesthesiol., 2005, September, 19(3), pp. 381-9; and Rudolph U & Antkowiak B., *Molecular and neuronal substrates for general anaesthetics*, Nat Rev Neurosci., 2004, September, 5(9), pp. 709-20). Being able to non-invasively quantify both the levels of hypnosis and analgesia is of great clinical utility, as separate measures have important implications in terms of subsequent and ongoing clinical management and clinical outcome. For example, detecting adequate analagesia is important for achieving physiological (autonomic) stability during surgical procedures, and helps improve postoperative clinical outcomes. Quantifying the magnitude of subcortical input may provide one way of assessing the level of analgesia by monitoring the degree to which peripherally derived sensory information reaches cortex.

Figure 2:
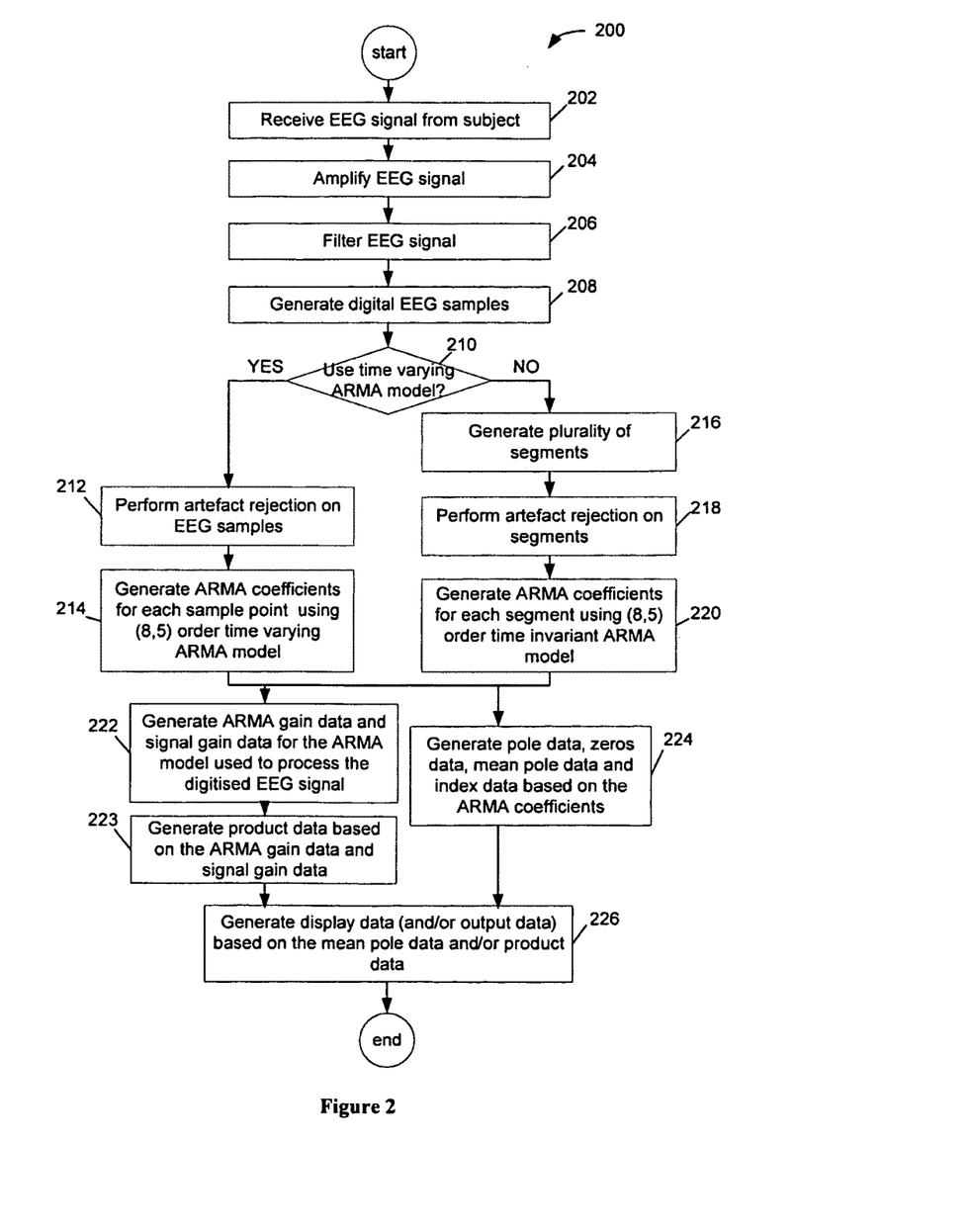
FIG. 2 is a flow diagram of the steps performed under the control of the EEG processing system.

FIG. 2 is a flow diagram of an EEG analysis process 200 performed by the EEG processing system 100. Process 200 begins at step 202 with the signal processing module 106 receiving an EEG signal from the subject via the electrodes 102. At step 204, module 106 amplifies the EEG signal. At step 206, module 106 filters the EEG signal using a band-pass filtered to remove low frequency movement artefact, EMG components and main artefacts (generally arising between 0 Hz to 50-60 Hz), as well as other sources of external noise. At step 208, module 106 converts the EEG signal into digital EEG samples.

Step 210 decides how to process the EEG samples based on the user's selection. If the user selects a processing option for analysing the samples substantially in real-time, step 210 proceeds to step 212. Otherwise, a default processing option is selected and step 210 proceeds to step 216.

The response index calculation module 108 performs steps 212 and 214 in respect of each new sample point generated by the module 108. At step 212, module 108 performs additional artefact rejection on the EEG samples, including further removal of periodic 0 Hz to 50-60 Hz interference from the samples, which is known to compromise the subsequent estimation of AR and MA coefficients.

At step 214, module 108 generates coefficient data for each sample point representing the AR and MA coefficients for a time varying ARMA representation of the EEG signal for each window. For example, at step 214, module 108 generates the AR and MA coefficients directly from the EEG samples using a Kalman adaptive filtering method. In step 214, the coefficient data represents the optimal values of the AR and MA coefficients as described above. Step 214 then proceeds to step 222 and step 224, which are performed in parallel to each other.

At step 216, module 108 generates a plurality of segments, each representing a portion of the digital EEG signal for the same duration. For example, each segment may represent a 2-second sample of the EEG signal and may overlap with a portion of an adjacent segment. At step 218, module 108 filters each segment to remove additional artefacts from the signal, including removing periodic 0 Hz to 50-60 Hz interference which is known to compromise the subsequent estimation of AR and MA coefficients. At step 220, module 108 generates coefficient data based on the respective time invariant ARMA representation of the EEG signal (e.g. based on an (8,5) order ARMA representation) for each segment. The coefficient data can be generated using software, such as the functions associated with the MATLAB® System Identification Toolbox version 6.0). Step 220 then proceeds to step 222 and step 224.

At step 222, module 108 generates, for each segment/sample point, ARMA gain data representing an ARMA gain value (i.e. $\langle Y(t) \rangle$ in Equation 18) based on the corresponding ARMA representation used in step 214 or 220 for generating the coefficient data for the corresponding segment/sample point. This involves applying the estimated AR and MA coefficients to the corresponding ARMA representation (i.e. Equation 2 or Equation 10), and generating a signal representation (represented by y[n]) by driving the corresponding ARMA representation with a normalised white noise input (represented by u[n−k]).

At step 222, module 108 also generates, for each segment/sample point, signal gain data representing a signal gain value (i.e. $\langle \tilde{Y}(t) \rangle$ in Equation 18) based on the EEG samples for the corresponding segment, in the case where a time-invariant ARMA representation is used (at steps 216, 218, and 220), or for a range of EEG sample values in the case where a time varying ARMA representation is used (at steps 212 and 214). The value of $\langle \tilde{Y}(t) \rangle$ for each sample point is generated based on an appropriate portion of the detected EEG signal either centred on the time at which the coefficient data for the corresponding sample point was generated, or generated based on an appropriately constructed average of the sampled EEG signal including and prior to the current sample point. Alternatively, a value of $\langle \tilde{Y}(t) \rangle$ is generated based on each respective segment generated by module 108 at step 216.

At step 233, module 108 then generates, for each segment/sample point, product data representing the value of the product $g(q)P(\omega)$ according to Equation 18 based on the corresponding ARMA gain data and signal gain data. Changes in the value of the $g(q)P(\omega)$ represents changes in the magnitude of the subcortical input (represented by $P(\omega)$).

Step 224 generates poles data and zeros data based on Equations 9 and 10, and then module 108 generates mean pole data based on Equation 12 representing the unscaled mean pole position for each respective segment/sample point. Module 108 then generates index data based on Equations 13 or 14 representing a scaled numeric representation of the mean pole position for the corresponding segment/sample point.

Steps 223 and 224 proceed to step 226, where the display module 114 generates display data representing user interfaces based on brain state data (e.g. using the poles data, zeros data, mean pole data, index data and/or product data), and preferably including a representation of the EEG samples, to represent functional state of the subject's brain and/or level of subcortical activity in the subject's brain. Step 226 also controls the data export module to generate output data including data representative of the EEG samples, brain state data, raw mean pole data and/or scaled mean pole data. Process 200 ends after step 226.

Changes in the value represented by the scaled mean pole data (or unsealed mean pole data) represent changes in the functional state of the subject's brain (i.e. how the brain responds to cortical input). Changes in the value represented by cortical input data represent changes in value of the product $g(q)P(\omega)$ and thus the level of brain cortical input. An advantage provided by the ARMA gain, and hence a measure of subcortical input, is to enhance the physiological specificity (and hence clinical utility) of the determination of the subject brain function.

Many modifications will be apparent to those skilled in the art without departing from the scope of the present invention as herein described with reference to the accompanying drawings.

The reference to any prior art in this specification is not, and should not be taken as, an acknowledgment or any form of suggestion that that prior art forms part of the common general knowledge in Australia.

What is claimed:

1. A method for displaying the activity of a brain, the method including the steps of:
   (i) obtaining an electroencephalogram (EEG) signal from the brain;
   (ii) segmenting said EEG signal with a processor into either contiguous or overlapping segments comprised of a sequential number of samples of said EEG signal;
   (iii) representing said EEG segments as a fixed order autoregressive moving average (ARMA) signal representation with an autoregressive order between 8 and 13 and a moving average order between 5 and 11;
   (iv) generating AR coefficient data and MA coefficient data for said segments of said EEG signal for said fixed order ARMA signal representation;
   (v) generating signal representations for said segments of EEG signal by substituting generated AR coefficient data and MA coefficient data for said segments of EEG signal into said fixed order ARMA representation, and providing as a driving input to said EEG signal representation a zero mean unit variance Gaussian random process;
   (vi) generating an ARMA gain value as the root mean square of the amplitude values for said signal representations for said segments of EEG;
   (vii) generating brain product data representative of input to cortex by dividing the root mean square of the amplitude of the EEG signal for said segments by the ARMA gain value for said signal representations of said EEG segments;
   (viii) displaying said brain product data on display means.

2. A method as claimed in claim 1 including the step of displaying to a user of the method on said display means an option to select a time varying or time invariant ARMA signal representation in step (iii).

3. A method as claimed in claim 2 including the steps of:
   (ix) selecting a fixed order time invariant ARMA signal representation of autoregressive order 8 and moving average order of 5;

$$y[n] = -\sum_{k=1}^{8} a_k y[n-k] + \sum_{k=0}^{5} b_k u[n-k]$$

where $y[n]$ represents an ordinal sequence of samples of said EEG signal, $y[n-k]$ represents the k-th prior sampled value of $y[n]$; $u[n-k]$ represents a Gaussian white noise process; and $a_k$ and $b_k$ represent the estimated autoregressive AR and moving average MA coefficients determined in step (iv) respectively for a said segment of said EEG signal.
   (x) estimating the autoregressive AR coefficients $a_1$-$a_8$ and moving average MA coefficients $b_0$-$b_5$ for the time invariant fixed order ARMA signal representation of the equation of step (ix) for one or more said EEG segments;
   (xi) substituting the estimated autoregressive AR and moving average MA coefficients of step (x) into the fixed order time invariant ARMA model of the equation in step (ix);
   (xii) generating an ARMA gain value $\langle Y(t) \rangle$ as the root mean square value of the amplitude values for said signal representations generated in step (xi) for said EEG segments;
   (xiii) estimating the input to cortex as the product $g(q)P(\omega)$ calculated using the equation $$g(q)P(\omega) = \frac{\langle \tilde{Y}(t) \rangle}{\langle Y(t) \rangle}$$

where $\langle Y(t) \rangle$ is the ARMA gain estimated in step (xii) above and $\langle \tilde{Y}(t) \rangle$ is the root mean square of the amplitude of said EEG segments.

4. A method as claimed in claim 2 including the steps of:
   (xiv) recursively estimating the autoregressive coefficients $a_1$-$a_8$ and moving average coefficients $b_0$-$b_5$ for each sample point n as $a_1^{(n)}$-$a_8^{(n)}$ and $b_0^{(n)}$-$b_5^{(n)}$ respectively so that the following fixed order time-varying ARMA representation of AR order 8 and MA order 5 will have been selected;

$$y[n] = -\sum_{k=1}^{8} a_k^{(n)} y[n-k] + \sum_{k=0}^{5} b_k^{(n)} u[n-k]$$

(xv) substituting the estimated autoregressive AR and moving average MA coefficients for each sample point n into the fixed order time varying ARMA model of the equation in step (xiv);
   (xvi) generating an ARMA gain value $\langle Y(t) \rangle$ for each sample point n as the root mean square value of the amplitude values for said signal representation generated in step (xv) for said sample point n;
   (xvii) estimating the input to cortex as the product $g(q)P(\omega)$ calculated using the equation $$g(q)P(\omega) = \frac{\langle \tilde{Y}(t) \rangle}{\langle Y(t) \rangle}$$

where $\langle Y(t) \rangle$ is the ARMA gain estimated in step (xvi) above and $\langle \tilde{Y}(t) \rangle$ is estimated for each sample point n as either:

(a) the root mean square of a selected portion of the detected EEG signal centred on the sample point n at which the corresponding AR and MA coefficient data was generated; or (b) an average calculated for a selected portion of the sampled EEG signal including and prior to the current sample point n.

5. A method as claimed in claim 1 wherein step (viii) includes the step of displaying said brain product data in graphical form.

6. A method as claimed in claim 1 wherein step (viii) includes the step of displaying said brain product data in colours corresponding to different predetermined ranges of values of said brain product data, wherein each predetermined range is represented by a different colour.

7. A method as claimed in claim 1 wherein the displayed brain product data is scaled to fall within a predefined range.

8. A method as claimed in claim 1 wherein brain product data is represented as an index value.

9. A system for displaying activity of a brain, the system including a plurality of electrodes for picking up EEG signals from the brain of a subject; digitizing means for converting the EEG signals to a digitised EEG data signal; and computing means for:

(i) segmenting said EEG signal into either contiguous or overlapping segments comprised of a sequential number of samples of said EEG signal;

(ii) representing said EEG segments as a fixed order autoregressive moving average (ARMA) signal representation with an autoregressive order between 8 and 13 and a moving average order between 5 and 11;

(iii) generating AR coefficient data and MA coefficient data for said segments of said EEG signal for said fixed order ARMA signal representation;

(iv) generating signal representations for said segments of EEG signal by substituting generated AR coefficient data and MA coefficient data for said segments of EEG signal into said fixed order ARMA representation, and providing as a driving input to said EEG signal representation with a zero mean unit variance Gaussian random process;

(v) generating an ARMA gain value as the root mean square of the amplitude values for said signal representations for said segments of EEG;

(vi) generating brain product data representative of input to cortex by dividing the root mean square of the amplitude of the EEG signal for said segments by the ARMA gain value for said signal representations of said EEG segments;

(vii) displaying said brain product data on display means.

10. A system as claimed in claim 9 wherein the computing means provides the user of the method an option to select a time varying or time invariant ARMA signal representation in step (ii).

11. A system as claimed in claim 10 wherein the computing means carries out the steps of:

(viii) selecting a fixed order time invariant ARMA signal representation of autoregressive order 8 and moving average order of 5;

$$y[n] = -\sum_{k=1}^{8} a_k y[n-k] + \sum_{k=0}^{5} b_k u[n-k]$$

where y[n] represents an ordinal sequence of samples of said EEG signal, y[n−k] represents the k-th prior sampled value of y[n]; u[n−k] represents a Gaussian white noise process; and $a_k$ and $b_k$ represent the estimated autoregressive AR and moving average MA coefficients determined in step (iii) respectively for a said segment of said EEG signal.

(ix) estimating the autoregressive AR coefficients $a_1$-$a_8$ and moving average MA coefficients $b_0$-$b_5$ for the time invariant fixed order ARMA signal representation of the equation of step (viii) for one or more said EEG segments;

(x) substituting the estimated autoregressive AR and moving average MA coefficients of step (ix) into the fixed order time invariant ARMA model of the equation in step (viii);

(xi) generating an ARMA gain value $\langle Y(t) \rangle$ as the root mean square value of the amplitude values for said signal representations generated in step (x) for said EEG segments;

(xii) estimating the input to cortex as the product $g(q)P(\omega)$ calculated using the equation $$g(q)P(\omega) = \frac{\langle \tilde{Y}(t) \rangle}{\langle Y(t) \rangle}$$

where $\langle Y(t) \rangle$ is the ARMA gain estimated in step (xi) above and $\langle \tilde{Y}(t) \rangle$ is the root mean square of the amplitude of said EEG segments.

12. A system as claimed in claim 10 wherein the computing means carries out the steps of:

(xiii) recursively estimating the autoregressive coefficients $a_1$-$a_8$ and moving average coefficients $b_0$-$b_5$ for each sample point n as $a_1^{(n)}$-$a_8^{(n)}$ and $b_0^{(n)}$-$b_5^{(n)}$ respectively so that the following fixed order time-varying ARMA representation of AR order 8 and MA order 5 will have been selected;

$$y[n] = -\sum_{k=1}^{8} a_k^{(n)} y[n-k] + \sum_{k=0}^{5} b_k^{(n)} u[n-k]$$

(xiv) substituting the estimated autoregressive AR and moving average MA coefficients for each sample point n into the fixed order time varying ARMA model of the equation in step (xiii);

(xv) generating an ARMA gain value $\langle Y(t) \rangle$ for each sample point n as the root mean square value of the amplitude values for said signal representation generated in step (xiv) for said sample point n;

(xvi) estimating the input to cortex as the product $g(q)P(\omega)$ calculated using the equation $$g(q)P(\omega) = \frac{\langle \tilde{Y}(t) \rangle}{\langle Y(t) \rangle}$$

where $\langle Y(t) \rangle$ is the ARMA gain estimated in step (xv) above and $\langle \tilde{Y}(t) \rangle$ is estimated for each sample point n as either:
- (a) the root mean square of a selected portion of the detected EEG signal centred on the sample point n at which the corresponding AR and MA coefficient data was generated; or
- (b) an average calculated for a selected portion of the sampled EEG signal including and prior to the current sample point n.

13. A system as claimed in claim 9, the display means displays said brain product data in graphical form.

14. A system as claimed in claim 9 wherein the computing means carries out step (vii) such that the brain product data is displayed in colours corresponding to different predetermined ranges of values of said brain product data, wherein each predetermined range is represented by a different colour.

15. A system as claimed in claim 9 wherein the displayed brain product data is scaled to fall within a predefined range.

16. A system as claimed in claim 9 wherein brain product data is represented as an index value.

* * * * *